United States Patent [19]

That et al.

[11] Patent Number: 5,391,146

[45] Date of Patent: Feb. 21, 1995

[54] MECHANISM FOR MANIPULATING THE DISTAL END OF A BIOMEDICAL DEVICE

[75] Inventors: Dai T. That, San Jose; Robert Woodard, Fremont, both of Calif.

[73] Assignee: Conceptus, Inc., Fremont, Calif.

[21] Appl. No.: 84,457

[22] Filed: Jun. 24, 1993

[51] Int. Cl.⁶ ............... A61M 37/00; A61M 25/00
[52] U.S. Cl. ........................ 604/95; 604/282; 128/772
[58] Field of Search ............ 604/95, 280, 282; 128/772, 657

[56] References Cited

U.S. PATENT DOCUMENTS

| | | | |
|---|---|---|---|
| 2,688,329 | 9/1954 | Wallace | 604/95 |
| 4,586,923 | 5/1986 | Gould et al. | 604/95 |
| 4,650,467 | 3/1987 | Bonello et al. | |
| 4,723,836 | 2/1988 | Buchbinder et al. | 604/95 |
| 4,732,163 | 3/1988 | Bonello et al. | |
| 4,734,093 | 3/1988 | Bonello et al. | |
| 4,787,399 | 11/1988 | Bonello et al. | |
| 4,798,598 | 1/1989 | Bonello et al. | |
| 4,898,577 | 2/1990 | Badger et al. | 604/95 |
| 4,906,230 | 3/1990 | Maloney et al. | 604/95 |
| 4,940,062 | 7/1990 | Hampton et al. | 604/95 |
| 5,168,864 | 12/1992 | Shockey | 604/282 |

FOREIGN PATENT DOCUMENTS 0090734  11/1937  Sweden ................ 604/95

*Primary Examiner*—John D. Yasko
*Assistant Examiner*—Adam J. Cermak
*Attorney, Agent, or Firm*—Townsend and Townsend Khourie and Crew

[57] ABSTRACT

A mechanism for manipulating the distal end of an elongate medical device, wherein steering is accomplished by a single wire which extends from the proximal to the distal end of the device, the wire being anchored at an eccentric location relative to the central axis of the device containing said steering mechanism. Advantageously, a device comprising the steering mechanism also comprises at least one through lumen extending substantially from the proximal to the distal end of the device whereby a device or materials can be moved to the distal end of the device.

18 Claims, 2 Drawing Sheets

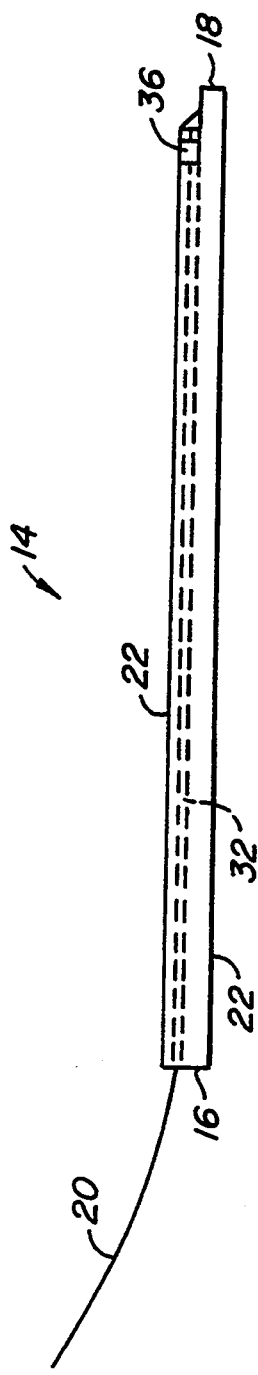
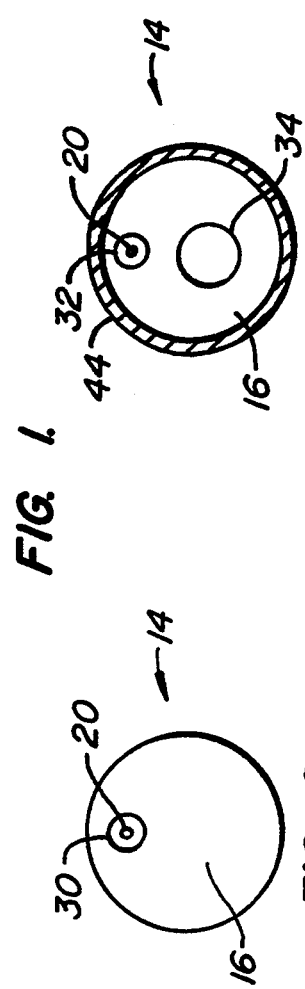
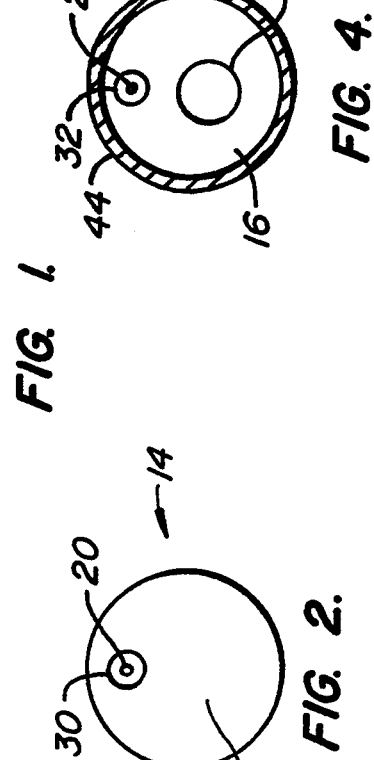
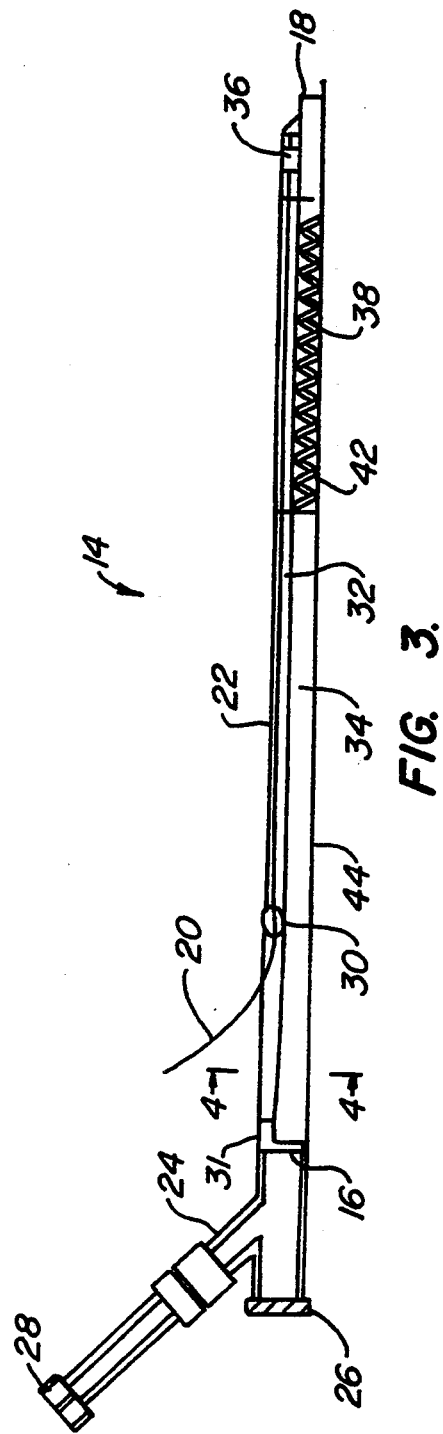

MECHANISM FOR MANIPULATING THE DISTAL END OF A BIOMEDICAL DEVICE

FIELD OF THE INVENTION

The present invention relates to biomedical devices, more particularly, the present invention relates to a mechanism for manipulating the distal end of catheter advantageously used for uterine cannulation.

BACKGROUND OF THE INVENTION

Previously, myriad devices have been developed for use in accessing and potentially visualizing sites within a body.

Many biomedical devices have mechanisms for manipulating the distal ends of the devices. Heretofore, the mechanisms for manipulating the distal ends of biomedical devices, by means at their proximal ends, have been based on the application of pulling force.

Single wire mechanisms for achieving distal manipulation of the device have been utilized. Such single wire devices can accomplish distal movement of a biomedical device only in a single direction relative to the central longitudinal axis. Thus, such single wire mechanisms have yielded movement only within one quadrant of a plane perpendicular to a plane corresponding to the longitudinal axis of the biomedical device. See, e.g., Bonello, et al., U.S. Pat. No. 4,734,093.

In order to accomplish effective distal movement of a device in more than one quadrant of a plane perpendicular to the longitudinal axis of a biomedical device, multiple wire mechanisms for achieving manipulation were employed. However, as with single wire mechanisms, multiple wire mechanisms achieve distal manipulation solely upon application of a pulling force. For example, two wires, each placed approximately 180° opposite one another, and running from the proximal to the distal end of a device, were constructed into a device so that the distal ends of the wires were anchored at or near the distal end of the device. Thus, pulling one wire would move the distal end of the device in the direction that wire was located. In contrast, pulling the opposite wire would cause movement of the distal end of the device in the direction that wire was located. Thereby, movement of the distal end of such a device was accomplished in the plane extending between the two distal attachment points of the two wires. Consequent to the size of dual wire mechanisms for manipulation, the size of such a device was enlarged relative to devices that are not distally manipulable or that have single wire mechanisms for manipulation. An additional issue with multi-wire devices is the cost of producing such intricate devices. Due to their complexity, the devices tend to be very expensive.

Thus, there has been a need for a relatively compact, manipulable and cost-efficient mechanism for manipulating the distal end of a device.

SUMMARY OF THE INVENTION

For the first time in the art, a compact, readily manipulable device, is set forth which provides for movement of the distal end of the device by means of a single wire mechanism; the device achieves movement through at least two quadrants of a plane perpendicular to the longitudinal axis of device. Typically, the movement is in quadrants that are bilaterally located with respect to the longitudinal axis of the device. The device has a further advantage of being produced in a cost-efficient manner.

Accordingly, a mechanism for manipulating the distal end of an elongate biomedical device is set forth. Typically, the device comprises an elongate shaft that has proximal and distal ends and that defines a lumen extending therethrough. The mechanism utilizes only one wire, the wire being located within the lumen of the shaft. The wire extends from the proximal end substantially to the distal end of the shaft. Additionally, the mechanism comprises a means for anchoring the distal end of the wire at substantially the distal end of the shaft. The means for anchoring is located eccentrically with respect to the central longitudinal access of the elongate device. Generally, the cross-sectional area of the lumen is between 120% to 400% of the cross-sectional area of the wire. However, a broader range of the cross-sectional area of the lumen relative to the cross-sectional area of the wire is applicable when alternate materials are utilized.

A device comprising the mechanism for manipulating the distal end of an elongate medical device is also set forth. A device in accordance with the invention can comprise one or more through lumens that extend substantially from the proximal to the distal end of the device. A device in accordance with the invention can have proximal and distal sections wherein different materials comprise the proximal and distal sections. A method for use of a device in accordance with the invention is also set forth. Advantageously, an embodiment of the device in accordance with the invention allows direct visualization of the uterus, as well as the os and proximal portions of the fallopian tubes.

BRIEF DESCRIPTION OF THE DRAWINGS

FIG. 1 illustrates a side view of an embodiment of the present invention.

FIG. 2 illustrates an end-on view of the proximal end of the embodiment illustrated in FIG. 1.

FIG. 3 illustrates a longitudinal section of an alternate embodiment of a device in accordance with the present invention.

FIG. 4 illustrates an end-on view of the proximal end of the embodiment illustrated in FIG. 3.

DETAILED DESCRIPTION OF THE INVENTION

Figure 5:
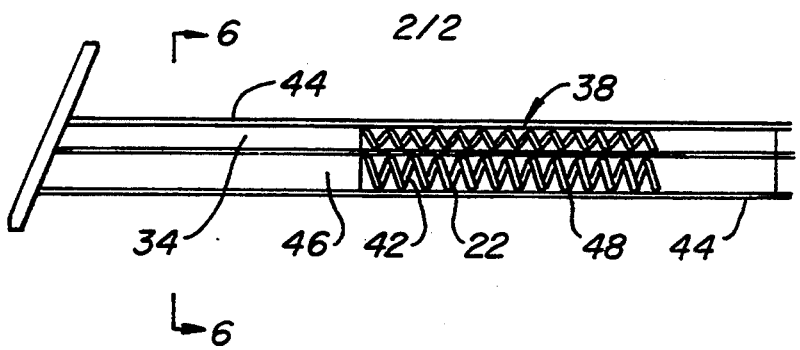
FIG. 5 illustrates a longitudinal section of the distal end of another alternate embodiment of a catheter in accordance with the present invention.

The present invention is a mechanism for manipulating the distal end of a biomedical device, whereby the distal end is moveable through at least two quadrants, and in ceratin embodiments more than three quadrants, of a plane perpendicular to the longitudinal axis of the device containing the mechanism. Typically, the movement is in quadrants that are bilaterally located with respect to the longitudinal axis of the device. The mechanism achieves such distal manipulation by means of a single wire guiding mechanism. In accordance with the present invention, distal manipulation of the device is achieved with the single wire by means of a push-pull action, in contrast to prior distally moveable devices which were typically manipulated by means of multiple wire mechanisms that effected movement only by pulling action.

A schematic of one embodiment of a device comprising the steering mechanism of the present invention illustrated in FIGS. 1 and 2.

As illustrated in FIG. 1, a device 14, in accordance with the invention, comprises a wire 20, and an elongate shaft 22. Device 14 has proximal end 16 and a distal end 18. Proximal end 16 is depicted in an end-on view in FIG. 2. As illustrated in FIGS. 1 and 2, device 14 is seen to have an aperture 30, which leads to a wire lumen 32. Wire 20 passes through aperture 30 and, as depicted in phantom lines in FIG. 1, passes through wire lumen 32. Wire 20 is attached near the distal end of the device by means of a wire anchor 36.

Referring again to FIGS. 1 and 2, it is seen that aperture 30, and, in a typical embodiment accordingly, wire lumen 32, is eccentrically placed with regard to the central longitudinal axis of device 14. Eccentric placement of anchor 36, relative to the central axis of the device, is an important feature leading to the advantageous function of the device. A second important feature which leads to the advantageous function of the device is the relative size of the inner diameter of wire lumen 32 relative to the outer diameter of wire 20. In a preferred embodiment, wire 20 is substantially round in cross-section, as illustrated in FIG. 2, and aperture 30 and wire lumen 32 extending therefrom is substantially round as well. For the preferred rounded configuration of the device, the inner diameter of wire lumen 32 is, typically, within a range of 110% to 200% of the size of the outer diameter of wire 20. Although rounded configurations of the wire and lumen are preferred, alternate configurations such as ovoid lumens or a ribbon-like wire are also used in accordance with the invention. Accordingly, the cross-sectional area of the lumen 32 is typically in a range of 120% to 400% of the cross-sectional area of the wire 20.

A device in accordance with the invention, such as illustrated in FIGS. 1 and 2 is preferably produced by extruding a polymer material having an eccentrically located longitudinal lumen 32. Typically, tubing such as polypropylene is utilized, although other biocompatible materials suitable for use in biomedical devices are used as well. Wire 20 is typically constructed of stainless steel material. Alternatively, other materials such as various metallic alloys, or wire materials constructed substantially entirely of polymer materials are used. Advantageously, the material utilized for wire 20 should be substantially non-compressible upon application of pushing axial force, the material should be substantially non-elongating upon application of pulling axial force, and should have the ability to flex relative to its longitudinal axis. Typically, wire anchor 36 is constructed of stainless steel and comprises an additional piece of wire wrapped around the distal end of wire 20. Alternatively, the anchor can comprise biocompatible adhesives or an additional aspect of wire 20 wherein, for example, wire 20 is wound upon itself. Accordingly, wire 20 is inserted through lumen 32 and is anchored at its distal end by means of anchor 36. Typically, the distal end of a polypropylene device is heated around stainless steel anchor 36, thereby securing the wire and sealing the distal end 18 of the device.

A device in accordance with that just described achieves, by application of pulling and pushing axial force on wire 20, movement of the distal end of the device through approximately 270° of a plane perpendicular to the longitudinal axis of the device.

The ratio of the cross-sectional area of lumen 32 and the cross-sectional area of wire 20 is important to the function of the invention since, should the cross-sectional area of the lumen be too large, undue flexing of wire 20 would occur within the shaft, and pushing force would not be transmitted along wire 20 to the distal end of the device. Alternatively, the cross-sectional area of lumen 32 must not be too small relative to the cross sectional area of wire 20, since, were the area of the lumen to be too small relative to the cross-sectional area of the wire, frictional forces would impede pushing forces on wire 20 from being transmitted to the distal end of the device. Although typical ranges for the cross-sectional area of wire 20 and the cross-sectional area of lumen 32 are provided, it will be appreciated by one of ordinary skill in the art, that alternate materials can be employed that allow the ratio range to be altered, as is appreciated by one of ordinary skill in the art. For example, particularly lubricious wire or materials comprising elongated shaft 22, and thus the walls of lumen 32, permit smaller ratios of the cross-sectional area of lumen 32 relative to the cross-sectional area of wire 20; alternatively, a more rigid wire can permit a larger ratio of the cross-sectional area of lumen 32 relative to the cross-sectional area of wire 20.

In accordance with device 14, as described above, application of pushing or pulling forces to wire 20 produces movement in a plane perpendicular to the longitudinal axis of the device, additionally, movement occurs on a plane corresponding to the longitudinal axis of the elongate device, since flexing of the device occurs throughout the length of the shaft 22. Preferably, differing degrees of flexibility are present along shaft 22. Differing degrees of flexibility along shaft 22 allows the movement in the plane corresponding to the longitudinal axis to be controlled. Flexibility can be affected by adding a material to certain regions of the shaft to decrease flexibility of the shaft. Typically, it is preferable that the shaft is less flexible in its proximal portions. Accordingly, means can be utilized to effect enhanced flexibility. Typically, it is preferred that the distal portions of the device be more flexible. One means by which the proximal area of the device is less flexible relative to the distal end is to use different materials for proximal and distal portions of the device, materials having substantially identical dimensions, but different properties of flexibility. Such fused materials would have substantially the same outer cross-sectional shape, and substantially the same inner diameter of lumen 32. The various materials comprising the device are fused in accordance with methodologies known to those of ordinary skill in the art. Alternatively, as a means to achieve enhanced flexibility, selected regions of the elongated shaft can be physically altered. For example, regions of the shaft, typically the distal portion, can be altered by scoring or cutting of ridges into such portions. Alternatively, to achieve decreased flexibility, a material can be embedded within selected portions of elongated shaft 22. For example, a metallic coil, not illustrated, is be embedded in selected regions of elongate shaft 22. Although it is preferred that device 14 have a substantially uniform cross-sectional shape at any location along its elongate axis, decreased flexibility of the device can be achieved by applying materials such as an additional sheath, or an external coil, to selected regions of the device, thus yielding a different cross-sectional shape in the regions of device 14 having such externally applied materials.

An alternate embodiment of the invention is illustrated in FIG. 3. In accordance with the embodiment illustrated in FIG. 3, the device 14 has a proximal end 16 and a distal end 18. FIG. 4 illustrates a cross-sectional view along plane 4—4 of the embodiment illustrated in FIG. 3.

As shown in FIG. 3, end fitting 24 is optionally used in conjunction with a catheter of the invention to advantageously attach other biomedical devices to the present device, or to facilitate use of the present device in medical procedures.

As illustrated in FIG. 3, wire 20 enters an aperture 30 in elongate shaft 22; aperture 30 leads to a wire lumen 32. Optionally, the proximal end of wire lumen 32 is sealed by means, such as a polymeric plug 31. Axially extending port 26 and external port 28 lead to a through lumen 34. Through lumen 34 is open at proximal end 16 and distal end 18 of the device.

Referring again to FIG. 3, wire 20 is seen to be embedded in the distal end of wire lumen 32 via anchor 36. Preferably, anchor 36 is constructed of a coil of wire material secured to the distal end of wire 20, although other anchoring mechanisms can be used, as noted above. Wire 20 is preferably constructed of stainless steel. As shown, wire 20, together with wire anchor 36, serve to close the distal end of wire lumen 32. Preferably, wire 20 and anchor 36 are constructed in accordance with the materials and by means of the methodologies listed above.

Typically, wire 20 has a diameter of between 0.001 to 0.030 mils. In a preferred embodiment, the wire has a diameter of 0.018 inches until approximately the distal 5 to 10 cm of the wire, where the wire begins to taper gradually to a diameter of 0.002 inches; with the preferred tapered wire, the outer diameter of anchor 36 is 0.007 inches. Although a gradually tapered wire is preferred, wires that taper in a step-wise manner are also useful, as is appreciated by those of ordinary skill in the art.

As illustrated in FIG. 3, a patency coil 38 is located near the distal end of the device, the patency coil surrounding lumen 34. Preferably, lumen 34 is essentially circular in cross-section, as shown in FIG. 4. Coil 38 enables lumen 34 to retain its preferred circular cross-sectional aspect, even when the wall that defines the lumen is flexed. Patency coil 38 is preferably constructed of stainless steel or platinum, although materials such as polymers or other metals can be used. Furthermore, although a coil for retaining patency has been illustrated, other material such as a coaxial sheath may also be used; alternatively, a polymer which retains patency and yet is flexible can also be used.

A device in accordance with the embodiment of the present invention illustrated in FIGS. 3 and 4 is preferably made according to the following methodology.

The device illustrated in FIGS. 3 and 4 contains a proximal portion which extends from the proximal end of the device to the proximal end of patency coil 38 and a distal portion of the device, extending from the proximal portion of patency coil 38 to the distal end of the device. In a preferred mode of manufacture, the proximal portion of the device is constructed by laying together a tube which will define wire lumen 32 and a tube which will define through lumen 34. The tubes that will yield wire lumen 32 and through lumen 34 are preferably constructed of polypropylene and have a length that corresponds to the eventual proximal portion of the device. Thereafter, it is preferred that the tubes be encased in a polyethylene sleeve 44. Accordingly, polyethylene sleeve 44, having a length that substantially corresponds to the length desired for the total length of the device, is pulled over the tubes that will yield wire lumen 32 and through lumen 34. Sleeve 44 is then heat attached over the tubes substantially along the entire proximal portion of the device, such as by heat shrinking. Typically, heat shrinking the polyethylene causes the preferred polypropylene tubes that will yield wire lumen 32 and through lumen 34 to melt together. Heat shrinking of sleeve 44 over the tubes occurs to a point at or near the junction between the proximal and distal portions of the device. At this stage in the preferred manufacturing process, sleeve 44 continues on past the distal end of the proximal portion. The non-fused portion of sleeve 44 is then manipulated in a way so that a patency coil is attached at the distal end of through lumen 34. The patency coil has an inner diameter that substantially corresponds to the inner diameter of through lumen 34. A filler material 42 is now added within sleeve 34 throughout the distal portion of the device. Preferably, filler material 42 comprises a material composed of a polymer that is springy and biologically compatible such as polyurethane, a block copolymer of polyamide, polyvinyl chloride, or silicone, or blends of such polymers. Patency of wire lumen 32 and through lumen 34 is accomplished according to methodologies known to those of ordinary skill in the biomedical device art. Thereafter, wire 20 is inserted through wire lumen 32. Typically, the distal end of wire lumen 32 is sealed by placing a small section of polypropylene at the distal-most end of the device. Thereafter, the small section of polypropylene at the distal-most end of the device is preferably heat shrunk onto wire anchor 36.

Typically, the device in accordance with the embodiment illustrated in FIGS. 3 and 4 is 10 to 25 inches in length and preferably about 20 inches in length. The distal portion of the device typically comprises the distal 0.25 to 3 inches, and most preferably about 1.5 inches of the device. Accordingly, the proximal portion of the device constitutes that portion of the device not constituted by the distal portion.

A device constructed in accordance with the invention as described is advantageous for use in biomedical procedures since the proximal portion preferably comprises a material which has qualities of flexibility, yet is rigid enough to facilitate pushing of the device without undue compression; alternatively, a highly flexible and springy polymer is advantageous as a component comprising the distal portion of the device due to its flexibility in the region of the device where distal movement is most desired. Furthermore, sleeve 44 is advantageous in that it provides a smooth outer surface along the device from its proximal end 16 to its distal end 18. In particular, it is advantageous that sleeve 44 provides a smooth surface at the transition between the proximal and distal portions of the device, near the junction of the patency coil and the material which comprises the proximal portion of the device. As an advantage of the steering mechanism, employing a single wire, a device is produced which has a relatively small cross-sectional diameter. Additionally, the through lumen of this embodiment permits materials to be introduced at the proximal end and released at the distal end of the device. In a particularly advantageous use of the device, a visualizing mechanism, such as a fiber optic mechanism, is introduced at the proximal end of the through lumen and advanced until it is at or near the distal end of the device. In an alternate embodiment of the device, to be discussed below, a second through lumen is also present. The second through lumen facilitates use of a cleansing fluid, to cleanse the optics of a mechanism that may have been introduced through the other through lumen. Advantageously, an embodiment of the device in accordance with the invention allows direct visualization of the uterus, as well as the os and proximal portions of the fallopian tubes.

Figure 6:
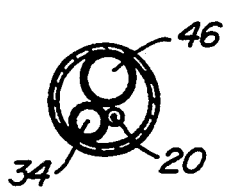
FIG. 6 illustrates a cross-sectional view taken along line 6—6 of FIG. 5.

FIG. 5 depicts, in longitudinal section, the distal end of an alternate embodiment of elongate shaft 22 of device 14. FIG. 6 depicts the embodiment of FIG. 5 in cross-section along plane 6—6. In the embodiment of FIGS. 5 and 6, two through lumens 34 and 46, lumens which substantially extend from the proximal to the distal end of the device, are present. A device having two such through lumens is constructed in accordance with the methodology employed to construct a device having a single through lumen. In addition, however, a second tube which will eventually define second through lumen 46 is utilized. The tube that will define second through lumen 46 is preferably constructed of the same materials that are utilized in the construction of the tube that gives rise to through lumen 34. A second patency coil 48 is used with the embodiment of FIGS. 5 and 6, the inner diameter of second patency coil 48 substantially corresponds to the cross-sectional diameter of second through lumen 46, analogous to the dimensional correspondence of patency coil 38 with regard to lumen 34. In a preferred embodiment having two through lumens, as with the single through lumen embodiment, flexible filler materials are preferably utilized over the distal portion, and a sleeve 44 is preferably heat shrunk over the outer surface of the device, to yield a preferred smooth transition along the outer surface of the device from its proximal to distal ends. Preferably, filler 42 is utilized in the distal portion of the embodiment illustrated in FIG. 5, the portion of the device comprising coils 38 and 48.

In a preferred embodiment of the device illustrated in FIGS. 5 and 6, through lumen 34 has an inner diameter of between 0.030 to 0.040 inches, preferably 0.034 inches; second through lumen 46 has an inner diameter of from 0.045 to 0.055 inches; and the cross-sectional diameter of the entire device when encased in sleeve 44 is from 0.105 to 0.115 inches, most preferably about 0.110 inches.

In the embodiment of device 14 illustrated in FIG. 3, the proximal end of wire 20 is accessible to the healthcare worker for use in manipulating the distal end of the device. An alternate embodiment of the proximal end of the device, for steering the distal end of the device, is illustrated in FIG. 7.

Figure 7:
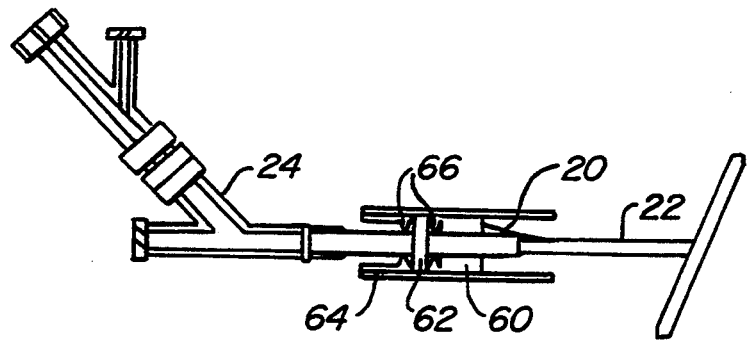
FIG. 7 illustrates the proximal end of one embodiment of a catheter in accordance with the present invention.

As depicted in FIG. 7, wire 20 is attached to a proximal anchor 60. Preferably, proximal wire anchor 60 is constructed of stainless steel and is shaped in a manner such that the proximal end of wire 20 is held between anchor 60 and guide 64 by interference fit. Alternate attachment mechanisms, such as soldering or gluing, are also used. Adjacent proximal wire anchor 60 is an O-ring 62. The inner diameter of O-ring 62 substantially corresponds to the outer diameter of elongate shaft 22.

The O-ring 62 is preferably held in its position relative to guide 64 by ridges 66 of the guide, additionally, the O-ring 62 and the proximal wire anchor 60 are preferably attached to one another with guide 64. As is appreciated by those of ordinary skill in the art, guide 64 is constructed of materials which are suitable for biomedical devices and is of a form that connects anchor 60 and O-ring 62 in a substantially rigid manner. Thus, movement of guide 64 moves O-ring 62 to a new location along shaft 22, and consequent to the substantially rigid attachment between O-ring 62 and anchor 60, results in a new position of wire 20, and, accordingly, a new position of the distal end of the device. Advantageously, friction between the inner diameter of O-ring 62 and the outer surface of elongate shaft 22 is sufficient to retain the O-ring, and accordingly, the entire mechanism for steering of wire 20, in the position along the shaft at which it is placed by the healthcare worker.

Figure 8:
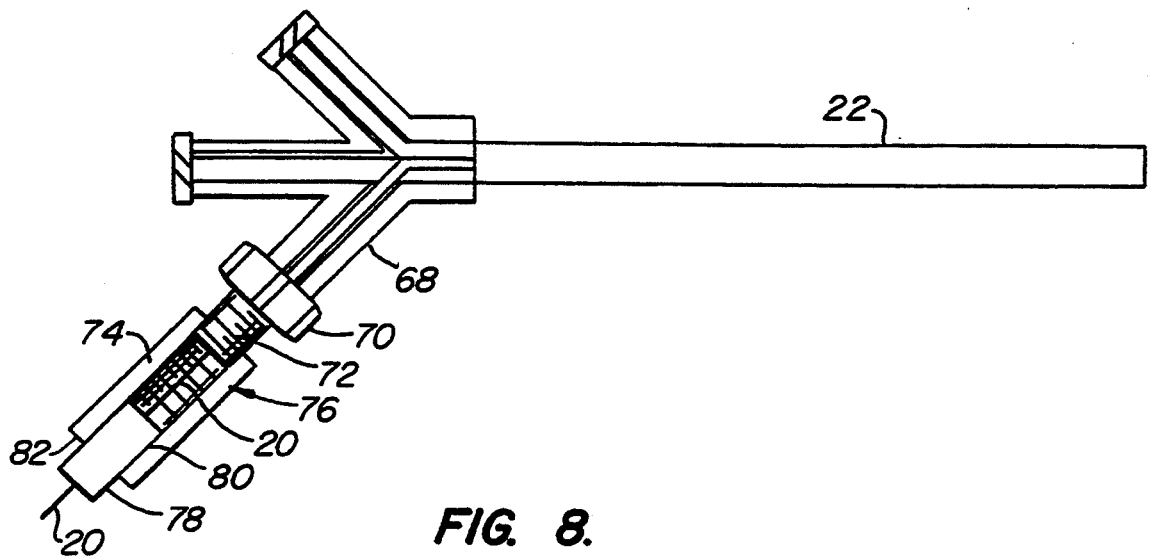
FIG. 8 illustrates the proximal end of an alternate embodiment of a catheter in accordance with the present invention.

An alternate mechanism located at the proximal end of the device for steering the distal end of the device via wire 20 is illustrated in FIG. 8. The embodiment in FIG. 8 utilizes a screw-type mechanism. Accordingly, an externally threaded component 70 is secured, according to methods readily appreciated by those of ordinary skill in the art, to a proximal end fitting, analogous to end fitting 24, illustrated in FIG. 3. However, as illustrated in FIG. 8, a branch 68 of the fitting contains an internal channel that leads to wire lumen 34. Threaded component 70 has threads 72 which are formed in a spiral manner. As further illustrated in FIG. 8, an internally threaded guide 74 has threads 76 which correspond to the threads 72 of threaded component 70. Thus, twisting movement of guide 74 causes movement between guide 74 and threaded component 70. As illustrated in FIG. 8, wire 20 is securely fastened to guide 74 by outer anchor 78 and inner anchor 80 where wire 20 extends through inner anchor 80, through the proximal end 82 of guide 74, through outer anchor 78, and continues to extend proximally. However, other mechanisms for rigidly securing wire 20 to guide 74 are available, such as soldering or use of adhesives, as is readily appreciated by one of ordinary skill in the art. Accordingly, due to the secure attachment of wire 20 to guide 74, movement of guide 74 relative to threaded component 70 causes wire 20 to be moved, and distal movement of the device results. Preferably, the frictional interaction between threads 76 and threads 72 is sufficient to retain wire 20 in the position that is achieved when the healthcare worker has twisted guide 74. Accordingly, the distal end of the device will retain the shape it has assumed.

It must be noted that as used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the presently preferred methods and materials are now described. All publications mentioned herein are incorporated herein by reference to describe and disclose specific information for which the reference was cited in connection with. All examples herein are provided for the purposes of illustration and clarification. It is understood that the invention is limited solely by the following claims.

What is claimed is:

1. A device having a mechanism for manipulating its distal end, comprising:
   an elongate shaft having proximal and distal ends and a wire lumen extending therethrough;
   only one wire, the wire within the wire lumen of the shaft, the wire having proximal and distal ends, wherein the wire substantially extends from the proximal to the distal ends of the shaft and wherein the wire lumen has a cross-section area, and the wire has a cross-sectional area, wherein the cross-sectional area of the wire lumen is in between 120% to 400% of the cross-sectional area of the wire over the entire length of the lumen; and
   a means for anchoring the distal end of the wire at substantially the distal end of the shaft, the means for anchoring located eccentrically with respect to the central longitudinal axis of the elongate device, such that the distal end of the device is deflected in a first direction by pulling on said only one wire and deflected in a second direction opposite to said first direction by pushing on said only one wire.

2. The device of claim 1 wherein the cross-sectional shape of the wire lumen is substantially round and the cross-sectional shape of the wire is substantially round.

3. The device of claim 1 wherein the wire is composed of stainless steel.

4. The device of claim 1 wherein the wire is composed of a polymer.

5. The device of claim 1 wherein the shaft has an elongate through lumen extending substantially from the proximal to the distal end of the device.

6. The device of claim 7 wherein the shaft has at least one additional elongate through lumen.

7. The device of claim 5 further comprising a means for retaining the patency of the through lumen.

8. The device of claim 7 wherein the means for retaining patency is a coil.

9. The device of claim 1 wherein the elongate shaft is elongate body comprising a proximal and a distal section, wherein the proximal section is substantially constructed of a first material, and the distal section is substantially constructed of a second material.

10. The device of claim 9 wherein the first material and the second material are the same material.

11. The device of claim 9 wherein the first material and the second material are different materials.

12. The device of claim 11 wherein the first material comprises polypropylene.

13. The device of claim 11 wherein the second material is more flexible than the first material.

14. The device of claim 1 wherein the elongate shaft has a flexible outer sleeve.

15. The device of claim 14 wherein the outer sleeve comprises polyethylene.

16. A method for accessing a site within a body, comprising
   introducing a distal end of a device to said site, said device having at least one through lumen to provide access;
   deflecting the distal end of the device in a first direction by pulling on a wire eccentrically attached to the distal end, wherein the wire is constrained in a wire lumen having a cross-sectional area which is from 120% to 400% of the cross-sectional area of the wire; and
   deflecting the distal end of the device in a second direction opposite to the first direction by pushing on the wire, wherein the pulling step and pushing steps can occur in any order.

17. A method as in claim 16, wherein the through lumen is reinforced with a wire coil along at least a portion of its length.

18. A method as in claim 16, wherein the distal end is introduced into the uterus.

* * * * *